United States Patent
Raulet et al.

(10) Patent No.: US 11,040,936 B2
(45) Date of Patent: Jun. 22, 2021

(54) ORGANOMETALLIC COMPLEX, POWDER INTENDED FOR ANIMAL FEED AND PREPARATION METHODS THEREOF

(71) Applicant: PANCOSMA SA, Le Grand-Saconnex (CH)

(72) Inventors: Christelle Raulet, Saint Julien en Genevois (FR); Clémentine Oguey, Ependes (CH); David Bravo, Yverdon-les Bains (CH)

(73) Assignee: PANCOSMA SA, Le Grand-Saconnex (CH)

( * ) Notice: Subject to any disclaimer, the term of this patent is extended or adjusted under 35 U.S.C. 154(b) by 1032 days.

(21) Appl. No.: 14/398,698

(22) PCT Filed: May 2, 2013

(86) PCT No.: PCT/EP2013/059173
§ 371 (c)(1),
(2) Date: Nov. 3, 2014

(87) PCT Pub. No.: WO2013/164416
PCT Pub. Date: Nov. 7, 2013

(65) Prior Publication Data
US 2015/0093469 A1    Apr. 2, 2015

(30) Foreign Application Priority Data
May 2, 2012    (FR) ...................................... 1253991

(51) Int. Cl.
*C07C 229/76*        (2006.01)
*A23K 20/10*         (2016.01)
(Continued)

(52) U.S. Cl.
CPC ............ *C07C 229/76* (2013.01); *A23K 20/10* (2016.05); *A23K 20/142* (2016.05); *A23K 50/00* (2016.05); *A23K 50/10* (2016.05); *A23K 50/80* (2016.05)

(58) Field of Classification Search
CPC .... A23K 1/1634; A23K 20/142; A23K 50/00; A23K 50/80; A23K 50/10; A23K 20/10; C07C 229/76
See application file for complete search history.

(56) References Cited

U.S. PATENT DOCUMENTS 5,185,144 A * 2/1993 Koslow ................. A61K 31/28
                                                    424/66
6,458,981 B1 * 10/2002 Ashmead .............. C07C 227/16
                                                    556/116
(Continued)

FOREIGN PATENT DOCUMENTS

FR       2833187 A1    6/2003
FR       2843752 A1    2/2004
(Continued)

OTHER PUBLICATIONS

International Search Report dated Sep. 26, 2013, issued in corresponding application No. PCT/EP2013/059173.
(Continued)

*Primary Examiner* — Erik Kashnikow
*Assistant Examiner* — Assaf Zilbering
(74) *Attorney, Agent, or Firm* — Seckel IP, PLLC

(57) ABSTRACT

The invention relates to an organometallic complex of the amino acid/metal type. The complex is a crystalline plurimetal complex that can be obtained in the form of a homogeneous powder that can be used to optimise animal feed. More specifically, the invention relates to an organometallic complex that is characterised in that it is formed by at least one amino acid or amino acid derivative with at least
(Continued)

two different metals. The invention also relates to a powder comprising the organometallic complex of the invention, as well as to methods for preparing such a powder.

18 Claims, 1 Drawing Sheet

(51) Int. Cl.
    *A23K 50/10*     (2016.01)
    *A23K 50/80*     (2016.01)
    *A23K 20/142*     (2016.01)
    *A23K 50/00*     (2016.01)

(56) References Cited

U.S. PATENT DOCUMENTS

| | | | |
|---|---|---|---|
| 7,022,351 | B2 | 4/2006 | Abdel-Monem et al. |
| 2003/0175360 | A1* | 9/2003 | Luzzatti .......... A61K 31/00 424/653 |
| 2004/0137108 | A1 | 7/2004 | Abdel-Monem et al. |

FOREIGN PATENT DOCUMENTS

| | | |
|---|---|---|
| WO | 83/01559 A1 | 5/1983 |
| WO | 03/049850 A2 | 6/2003 |
| WO | 03/072048 A2 | 9/2003 |

OTHER PUBLICATIONS

Gingaşu, Danna, et al., "Copper ferrite obtained by tow ' 'soft chemistry' ' routes", Journal of alloys and Compounds, Elsevier Sequoia, Lausanne, Switzerland, Nov. 30, 2006, vol. 425, No. 1-2, pp. 357-361, cited in ISR.
McArdle, Normat. T., et al., "Ultrastructual Studies of the Effects Produced by Some Amino Acid Metal Systems on *Escherichia coli* B", Inorganica Chimica Acta, Elsevier BV, Netherlands, 1984, vol. 92, No. 2, pp. 113-121, cited in ISR.
Bunel, C. et al., "Origin of Chirality in Charge Transfer Bands of Cu (II) Acidates", Journal of Inorganic and Nuclear Chemistry, Pergamon Press, United Kingdom,1981, vol. 43, pp. 971-975, cited in ISR.
European Office Action dated Dec. 5, 2017 in corresponding European application No. EP13722343.4 (with English machine translation; 11 pages).
Toyota et al., "A Rock-Salt-Like Lattice Structure Consisting of Monocationic and Monoanionic AuIAgICuIISupramolecular Cages of D-Penicillaminate", Angew. Chem. Int. Ed., vol. 44, No. 7, Feb. 4, 2005, pp. 1088-1092 (in English; cited in the European Office Action).
Kaiwar et al., "Synthesis, characterization and DNA interaction studies of CrIII products isolated from CrVI reduction with—SH containing molecules", Polyhedron, vol. 15, No. 5-6, Mar. 1, 1996, pp. 765-774 (in English; cited in the European Office Action).
EP Communication of Third Party Observations dated Apr. 9, 2020 in counterpart European application No. EP13722343.4 (observations in English; with English machine translation of cover page; total 4 pages).

* cited by examiner

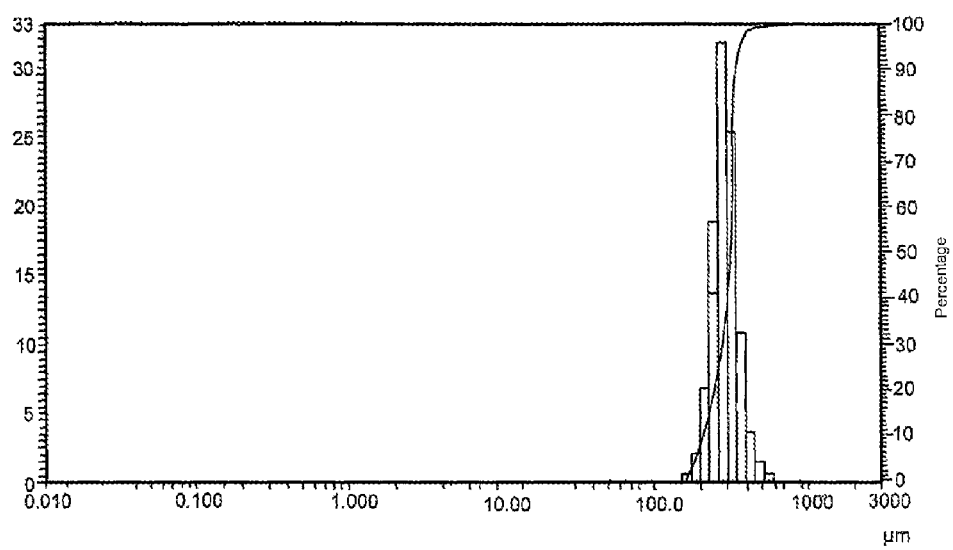

ORGANOMETALLIC COMPLEX, POWDER INTENDED FOR ANIMAL FEED AND PREPARATION METHODS THEREOF

The invention relates to an organometallic complex of the amino acid/metal type. This complex is polymetallic, it can be crystalline and can be obtained in the form of a homogeneous powder which makes it possible to optimize the feeding of animals. The invention also relates to processes for preparing such a powder.

BACKGROUND OF THE INVENTION

Currently, in order to supplement the diet of animals with metals such as iron, copper, zinc or manganese, certain compounds are added thereto. These compounds can be provided in an organic or complex form, which is more bioavailable than inorganic forms. They are used in powder or liquid form and mixed at low dose with animal feed in order to reequilibrate or adjust feed intakes or supplements with respect to trace elements.

Such compounds are the subject of the French patent application published under number FR 2 833 187. They are in the form of a complex of an amino acid with a metal sulfate. One of the objectives targeted on page 4, lines 3 to 6 of said document is to obtain grains in the form of crystals. According to one application mentioned on page 4, lines 14 to 16 of said document, the compound consists of water and a 1:1 complex of amino acids and of one of the following metals or a sulfate of one of the following metals: Cu, Co, Ca, Mg, Mo, Fe, Zn, Cr and Mn. The examples describe the preparation of compounds based on Zn, Cu, Fe or Mn. Claim 11 implies that certain Zn-based compounds are of the organometallic polymer type.

The international application published under number WO 03/049850 describes the preparation of Mg, Co, Fe, Mn, Cu or Zn glycinates.

Each of the compounds described in said documents provides a single metal. This means that a different compound corresponds to each metal and implies that it is necessary to carry out several individual additions and therefore as many separate quantitative determinations in order to obtain a feed intake which is supplemented and equilibrated with respect to several metals. Consequently, the homogeneity of the compounds in the intake is not necessarily totally optimal. Furthermore, this supposes that it is necessary to have available stocks of each of the compounds and logistics in accordance therewith.

SUMMARIZING DESCRIPTION OF THE INVENTION

The aim of the invention is, in particular, to simplify and optimize the homogeneity of the trace elements supplementation of animal feed intakes and to reduce the corresponding logistics.

According to the invention, this aim is achieved by replacing the use of several compounds each providing a metal, with the use of a single compound which on its own provides all the desired metals, in the desired proportions. This is obtained by virtue of an organometallic complex of the amino acid/metal type, characterized in that it consists of at least one amino acid or amino acid derivative with at least two different metals.

Thus, only one quantitative determination and one addition are now necessary in order to prepare the animal feed intake. Furthermore, there is now only one compound to be stored.

Moreover, this process makes it possible to optimize the ratios of trace elements to be supplemented within the same particle, and therefore not only makes it possible to as correctly as possible homogenize the minerals and their ratios, but might also make it possible to reduce as much as possible any antagonisms between minerals.

According to another aspect, the invention relates to a powder containing particles each comprising at least one organometallic complex according to the invention.

According to yet another aspect, the invention relates to a first process for preparing the abovementioned powder, in which:

a) a first aqueous solution of at least one amino acid or amino acid derivative and of at least one first metal is prepared;
b) a second aqueous solution of at least one amino acid or amino acid derivative and of at least one second metal is prepared;
c) step a) or b) is optionally repeated with other metals in order to prepare other aqueous solutions;
d) all the aqueous solutions prepared are mixed together;
e) a gaseous stream is produced;
f) the mixture obtained in step d) is sprayed into the gaseous stream; and
g) the powder obtained is recovered.

Of course, the same amino acid or amino acid derivative as in step a) can be used in step b) and/or in step c).

According to one variant, the powder according to the invention is prepared according to the following second process:

h) an aqueous solution is prepared in which at least one amino acid or amino acid derivative, at least one first metal and at least one second metal and, optionally, other metals, are mixed in the same container;
i) the mixture obtained in step h) is dried; and
j) the powder obtained is recovered.

The powder obtained by means of either of the processes according to the invention has the advantage of being homogeneous and crystalline.

Furthermore, it does not consist of particles comprising a first metal, particles comprising a second metal and, optionally, particles comprising a third metal, a fourth, etc., but of particles which each comprise, on their own, the first and second metals and, optionally, the third metal, the fourth, etc.

In steps d) and h) of the two processes above, a molar ratio of 1 between the amino acid(s) (and/or amino acid derivative (s)) and the metal is preferably chosen. For this, this ratio can be imposed in steps a) and b) and h) through the amount of products integrated into the mixture so as to form the aqueous solution(s).

Other characteristics and advantages of the invention will now be described in detail in the following description which is given with reference to the appended FIGURE which diagrammatically represents:

FIG. 1: a diagram representing the particle size distribution of the particles obtained using the process described in example 1.

DETAILED DESCRIPTION OF THE INVENTION

Complex According to the Invention

The complex according to the invention consists in at least one amino acid or amino acid derivative with at least two different metals.

As amino acids, mention may be made of methionine, lysine and glycine. It is the latter which is preferably chosen.

The term "amino acid derivative" is intended to mean particularly a hydroxy analog of an amino acid, for instance a hydroxy analog of methionine.

The metals are generally Cu, Co, Ca, Mg, Mo, Fe, Zn, Cr or Mn. Preferably, the two or more metals contained in the compound are chosen from the group consisting of Zn, Cu, Fe and Mn.

These metals can be initially bonded to a ligand optionally present in the complex. It is generally a sulfate, which can be bonded to a metal present in several possible oxidation states (Cu I or II, Fe II or III, etc.).

The compounds which have been found to be particularly advantageous are those based on glycine, on zinc sulfate, on copper sulfate, on iron sulfate or on manganese sulfate.

According to the invention, the ratios between the various weight contents of the metals can be very varied.

By way of example, mention may be made of a compound having the following weight ratios:
weight of Cu/weight of Fe: 0.1111
weight of Zn/weight of Fe: 0.8888
weight of Mn/weight of Fe: 0.5555.

One of the advantages provided by the invention is that it is possible to define, during the preparation of the complex, particular proportions of the metals that it is desired for said complex to contain. These particular proportions can be those required in order to cover the daily intakes required for a given animal, or else they can be fixed according to specifications provided by a user or for a special use.

Furthermore, the molar ratio between the amino acid(s) and/or amino acid derivative(s) and the metal is advantageously 1-to-1. Specifically, in the complex according to the invention, a metal is thus bonded to two amino acids (and/or amino acid derivatives) and one element of the amino acid and amino acid derivative group is bonded to two metals.

The result is therefore a molecule which is in the form of a chain alternating a metal and an amino acid or amino acid derivative. This molecule integrates the various metals chosen, in their initially predefined proportion.

Choosing a molar ratio of one to one between the metal and the amino acid (and/or derivative thereof) has the following advantages:
- this makes it possible to avoid obtaining a surplus of metals or of amino acids in the final complex, which would be free and might cause poor distribution of the metal in the product;
- this makes it possible to obtain 100% of active elements through the formation of a single compound;
- this makes it possible to obtain an economic advantage for the formulation, the preparation and the spraying, and facilitates its transportation.

Processes for Preparing the Powder According to the Invention a) First Preparation Process The powder according to the invention can be prepared according to the first process, which makes it possible to obtain it from multiple bases.

This process has the advantage that it can be carried out at ambient temperature.

The preparation of the aqueous solutions mentioned in steps a), b) and, optionally, c) is carried out in a manner known to those skilled in the art, for example according to the teachings of the abovementioned international application No. WO 03/049850 or of European patent application No. EP 2 843 752. The molar ratio of one metal to one element of the amino acid and/or amino acid derivative group is advantageously adhered to in these aqueous solutions.

The gaseous stream is advantageously a stream of air.

The spraying is carried out in a manner known to those skilled in the art.

b) Second Preparation Process

This process makes it possible to start from a single base.

The mixing of step h) can advantageously be carried out at ambient temperature.

The drying can be carried out in an incubator and in the open air.

Regardless of the process used, the respective proportions of the metals are advantageously chosen in such a way as to supplement the feed intake such that the latter covers the needs of the animal.

Furthermore, regardless of the preparation process used, the product obtained is in the form of a homogeneous powder consisting of particles resulting from a complexation of at least one amino acid with all the metals and their derivatives used.

In the particular case where glycine is used, the metals are organically bonded to the glycine. Specifically, the glycine is finally bonded to the metals via the two oxygens of its carboxyl group. Two different metals can thus be bonded to the same glycine. This is potentially advantageous since the absorption of each metal by the animal could be improved thereby. Furthermore, this polymer crystallizes in the form of a polymer crystal. This has the advantage of making it possible to identify its structure and optionally to improve its stability.

Uses

The powder according to the invention is intended for the feeding of animals, in particular ruminants, monogastric animals and aquaculture species.

It can be used in a proportion of from 1 to 1000 g per metric tonne of animal feed, either for the purpose of providing a daily intake of metals, for example, to promote the growth of the animal, or, in a more isolated manner, with a view to compensating for a metal deficiency observed in the animal, or in the context of a specific diet.

EXAMPLES

Example 1

In this example, a powder is prepared according to the first process, i.e. the process with multiple bases.

Aqueous solutions of Mn glycinate, Zn glycinate and Cu glycinate are prepared separately.

The 3 aqueous glycinate solutions are then combined in a single container and mixed.

The content of the container is then taken so as to be sprayed into a stream of air.

The equipment is adjusted so as to obtain a powder composed of particles of which the formulation after analysis is the following:

| Compound measured | Content as weight % in the particle |
| --- | --- |
| Zn sulfate•$H_2O$ | 40.83 |
| Mn sulfate•$H_2O$ | 23.11 |
| Cu sulfate•5 $H_2O$ | 6.67 |
| Glycine | 29.39 |
| Total | 100 |

The particle size distribution of the particles is represented on the diagram of FIG. 1. Its characteristic values are as follows:

10% of the particles have a size less than 164.42 µm;
the median size of the particles is 247.85 µm; and
90% of the particles have a size less than 388.29 µm.

X-ray diffraction analyses of the powder show that the product contains various crystalline structures.

Example 2

In this example, a powder was prepared according to the second process, i.e. the one with a single base.

An aqueous solution is prepared in which Mn sulfate, Fe sulfate, Zn sulfate, Cu sulfate and glycine are mixed in a container.

The base formulation is the following:

| Compound measured | Content as weight % |
| --- | --- |
| Fe sulfate•7 $H_2O$ | 24.32 |
| Zn sulfate•$H_2O$ | 15.09 |
| Mn sulfate•$H_2O$ | 14.68 |
| Cu sulfate•5 $H_2O$ | 20.96 |
| Glycine | 24.95 |
| Total | 100 |

The content of the container is dried in an incubator.

Crystals of 0.5 to 3 mm which are clearly visible to the naked eye (of the salt crystal type) are thus obtained. The crystalline structures are close to those of the particles of example 1.

The invention claimed is:

1. An organometallic complex consisting of at least one amino acid or amino acid derivative with at least two different metals, wherein the organometallic complex consists of:
at least two elements of the amino acid or amino acid derivative group, and
at least two different metals,
wherein the molar ratio of amino acid and/or amino acid derivative among the at least two elements of the amino acid or amino acid derivative group per metal anion the at least two different metals is 1-to-1,
wherein the organometallic complex is in the form of a chain alternating the metals and the amino acids,
wherein the metals are selected from the group consisting of zinc, copper, iron, manganese, cobalt, calcium, molybdenum, chromium and magnesium, and
wherein each of the metals among the at least two different metals is bonded to a ligand, wherein the ligand is a sulfate.

2. The complex as claimed in claim 1, wherein each metal of the organometallic complex is bonded to two elements of the amino acid and/or amino acid derivative group and each element of the amino acid and/or amino acid derivative group is bonded to two metals.

3. The complex as claimed in claim 1, which comprises an amino acid derivative which is a hydroxy analog of an amino acid.

4. The complex as claimed in claim 1, wherein one of the amino acids is glycine.

5. The complex as claimed in claim 4, wherein the glycine is bonded to two different metals via the two oxygens of its carboxyl group.

6. The complex as claimed in claim 1, consisting of (i) glycine and at least one selected from the group consisting of methionine and lysine, with (ii) zinc sulfate, copper sulfate, iron sulfate and manganese sulfate.

7. A powder comprising particles each comprising at least one organometallic complex as claimed in claim 1.

8. The powder as claimed in claim 7, wherein the respective proportions of the metals are chosen so as to promote the optimization of the daily intakes planned for an animal.

9. A process for preparing a powder, comprising:
a) preparing a first aqueous solution of at least one amino acid or amino acid derivative and of at least one first metal, the first aqueous solution comprising a molar ratio of amino acid and/or amino acid derivative per metal of 1-to-1;
b) preparing a second aqueous solution of at least one amino acid or amino acid derivative and of at least one second metal, the second aqueous solution comprising a molar ratio of amino acid and/or amino acid derivative per metal of 1-to-1;
c) optionally repeating step a) or b) with other metals in order to prepare other aqueous solutions;
d) mixing together all the aqueous solutions prepared;
e) producing a gaseous stream;
f) spraying the mixture obtained in step d) into the gaseous stream; and
g) recovering a powder obtained,
wherein the recovered powder is the powder as claimed in claim 7.

10. A process for preparing a powder, comprising:
h) preparing an aqueous solution in which at least one first amino acid or amino acid derivative, at least one second amino acid or amino acid derivative, at least one first metal and at least one second metal, optionally, other amino acid(s) or amino acid derivative(s), and, optionally, other metal(s), are mixed in the same container, the aqueous solution comprising a molar ratio of amino acid and/or amino acid derivative per metal of 1-to-1;
i) drying the mixture obtained in step h); and
j) recovering a powder obtained,
wherein the recovered powder is the powder as claimed in claim 7.

11. A method of feeding animals, comprising administering a powder as claimed in claim 7 to the animals.

12. The complex as claimed in claim 2, which comprises an amino acid derivative which is a hydroxy analog of an amino acid.

13. The complex as claimed in claim 2, wherein the amino acid is glycine.

14. The complex as claimed in claim 13, wherein the glycine is bonded to two different metals via the two oxygens of its carboxyl group.

15. The complex as claimed in claim 2, wherein the metals are chosen from the group consisting of zinc, copper, iron, manganese, cobalt, calcium, molybdenum, chromium and magnesium.

16. The complex as claimed in claim 3, which comprises an amino acid derivative which is a hydroxy analog of methionine.

17. The complex as claimed in claim 12, which comprises an amino acid derivative which is a hydroxy analog of methionine.

18. The complex as claimed in claim 1, wherein the metals are bonded to the elements of the amino acid or amino acid derivative group via at least one oxygen of a carboxyl group of the amino acid or amino acid derivative group.

\* \* \* \* \*